Jan. 11, 1966 J. GAUJARD Plant Pat. 2,586
ROSE PLANT
Filed Oct. 12, 1964
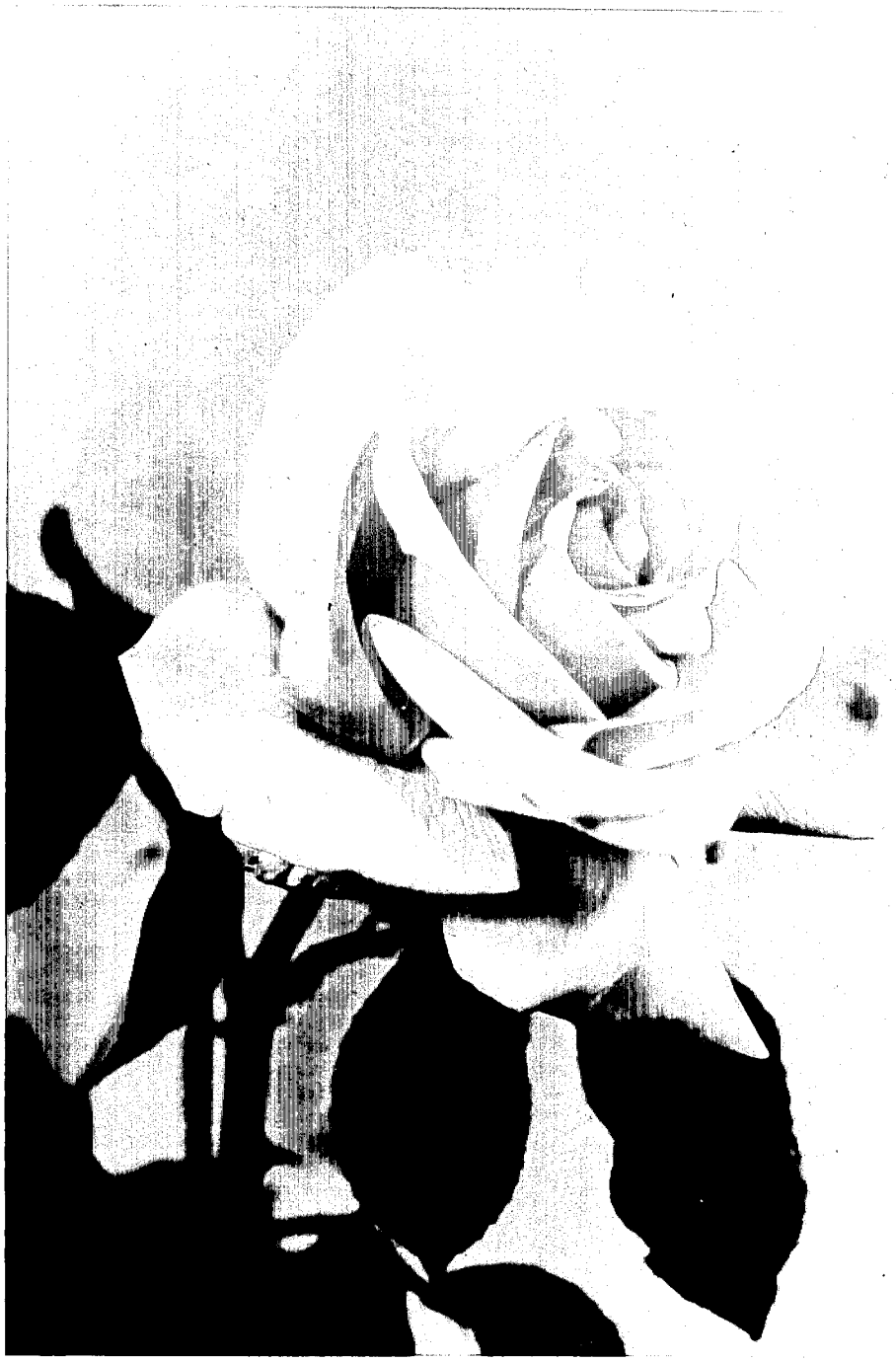
Inventor.
Jean Gaujard
By: Robb & Robb
Attorneys.

United States Patent Office

Plant Pat. 2,586
Patented Jan. 11, 1966

2,586
ROSE PLANT

Jean Gaujard, Feyzin, France, assignor to Ilgenfritz Nurseries, Inc., Monroe, Mich., a corporation of Michigan

Filed Oct. 12, 1964, Ser. No. 403,421
1 Claim. (Cl. Plt.—19)

The present invention relates to a new and distinct variety of rose plant of the hybrid tea class, which was originated by me by crossing the variety known as "Arles" (unpatented) with the variety known as "Mignonne" (U.S. Plant Patent No. 2,456).

As the result of this breeding, I have produced a new and improved rose variety which is distinguished from its parents, as well as from all other varieties of which I am aware, as evidenced by the following unique combination of characteristics which are outstanding therein:

(1) A vigorous habit of growth, exceeding that of the seed parent "Arles";
(2) A very free blooming habit;
(3) A two-toned appearance of the flower buds;
(4) Large size of the open flowers, exceeding that of the pollen parent "Mignonne";
(5) A satiny and hard texture of the flower petals; and
(6) A distinctive, attractive, soft but clear blending of the flower color from the tips of the petals to the base thereof when the buds open, with the color having the general appearance of one color, corresponding to Bright Carmine Rose when the flowers mature.

Asexual reproduction of the new variety by grafting, as performed by me at Feysin, France, shows that the aforementioned characteristics and distinctions come true to form and are established and transmitted through succeeding propagations.

The accompanying drawing shows typical specimens of the vegetative growth and flowers of my new variety as depicted in color as nearly true as it is reasonably possible to make the same in a color illustration of this character.

The following is a detailed description of my new variety, with color terminology in accordance with Robert F. Wilson's Horticultural Colour Chart, except where general color terms of ordinary dictionary significance are obvious:

Type: Hardy; outdoor; seedling; garden decoration.
Class: Hybrid tea.
Breeding: Seedling.
*Seed parent.*—"Arles".
*Pollen parent.*—"Mignonne".
Propagation: Holds its distinguishing characteristics through succeeding propagations by grafting.

*Flower*

Locality where grown and observed: Outdoors at Feyzin, France, and at Monroe, Michigan, U.S.A.
Flowers borne: Singly; on strong, long stems.
Quantity of bloom: Free, outdoors.
Continuity: Continuous.
Bud:
*Peduncle.*—Medium length; medium caliper; erect; stiff; with numerous red hairs. Color—Green Bronze.
*Before calyx breaks.*—Size—small. Form—short; pointed oval; without foliaceous appendages on the surface of the bud; without foliaceous parts extending beyond the tip of the bud. Color—Delft Rose, Plate 020/1.
*As a calyx breaks.*—Color—Delft Rose, Plate 020/1.
*As first petal opens.*—Size—large. Form—long; pointed. Color—outside: Geranium Lake, Plate 20/1; inside: Orient Red, Plate 819/3. Opening—opens up well.

Bloom:
*Size (when fully open).*—Large; from 5 inches to 5½ inches.
*Petalage.*—Double; from 35 to 40 petals; arranged regularly.
*Form.*—Full and high-centered at first and remaining high-centered; petals being at first tightly rolled outward and remaining tightly rolled outward at maturity.
Petals:
*Texture.*—Thick.
*Appearance.*—Inside—satiny. Outside—satiny.
*Shape.*—Outside—approximately oval, with apex having one notch. Inside—oval, with apex having one notch.

This description of a newly opened flower was made from a rose grown outdoors during the month of August at Monroe, Michigan, U.S.A.:

*Color.*—Outer petal—outside surface: Carmine, Plate 21/2, shading through Vermilion, Plate 18/1 to Lemon Yellow, Plate 4/1; inside surface: Carmine Rose, Plate 621/2, shading through Azalea Pink, Plate 618 to Lemon Yellow, Plate 4/1. Intermediate petal—outside surface: Carmine Rose, Plate 621/1, shading through Azalea Pink, Plate 618 to Sulphur Yellow, Plate 1; inside surface: Carmine Rose, Plate 621/2, shading through Shrimp Red, Plate 616 to Sulphur Yellow, Plate 1. Inner petal—outside surface: Porcelain Rose, Plate 621, shading to Shrimp Red, Plate 616 to Sulphur Yellow, Plate 1; inside surface: Empire Rose, Plate 0621/1, shading through Shrimp Red, Plate 616 to Sulphur Yellow, Plate 1.

This description of a rose that was open for three days outdoors during the month of August at Monroe, Michigan, U.S.A.:

*Color.*—Outer petal—outside surface: Carmine Rose, Plate 621/1, shading through Shrimp Red, Plate 616 to Sulphur Yellow, Plate 1/2; inside surface: Carmine Rose, Plate 621/1, shading through Shrimp Red, Plate 616 to Sulphur Yellow, Plate 1/2; inside surface: Carmine Rose, Plate 621/2, shading through Carrot Red, Plate 612/1, to Canary Yellow, Plate 2/1. Inner petal—outside surface: Geranium Lake, Plate 20/2, shading through Carmine Rose, Plate 621/1 to Aureolin, Plate 3/1; inside surface: Carmine Rose, Plate 621/2, shading through Vermilion, Plate 18/2 to Sulphur Yellow, Plate 1/2.
*General color effect.*—Newly opened flower—Carmine Rose, Plate 621/1 on the outer petals, and Jasper Red, Plate 018/1 on the inner petals. 3-days open—Carmine Rose, Plate 621/2.
*Behavior.*—Drop off cleanly; do not seem to be affected by cold, hot, wet or dry weather.
*Flower longevity.*—On bush in garden—5 days in August. Cut roses grown outdoors and kept at living-room temperatures—4 days in June.

*Reproductive organs*

Stamens: Very many; regularly arranged about pistils.
*Color.*—Red Bronze.
Filaments: From short to medium length; many with anthers.
*Color.*—Reddish.
Anthers: From medium to large size; open at various times.
*Color.*—Yellow.
Pollen: Sparse.

*Color.*—Gold.
Pistils: Many.
Styles: Uneven; short; very thin; bunched.
Stigma:
*Color.*—Red.
Ovaries: Some protruding from calyx.
Hips: Short; pointed; smooth.
*Color.*—Green.
Sepals: Long; spear-shaped; recurved.
Seeds: None observed.

*Plant*

Foliage:
*Leaves.*—Compound of 5 leaflets; normal abundance; medium-large size; glossy.
*Leaflets.*—Shape—oval, with apex acute. Base—from round to obtuse. Margin—simply serrate.
*Color.*—Mature—upper surface: Normal Green; under surface: Light Green. Young—upper surface: Light Bronze; under surface: moderately Dark Red.
*Rachis (the supporting stem of the compound leaf).*—Medium size. Upper side—hairy; grooved. Under side—moderately hairy.
*Stipules.*—From moderately short to medium length; wide; with points of medium length turning out at an angle of 45° and slightly recurved toward the stem.
*Disease resistance.*—Good resistance to mildew and blackspot, as determined by comparison with other varieties grown in France and at Monroe, Michigan, U.S.A., under the same cultural conditions.

Growth:
*Habit.*—Slightly sprawling.
*Growth.*—Moderately free.
*Canes.*—Heavy.
*Main stems.*—Color—Dull Bronze. Thorns—many; medium length; straight; with oval base. Prickles—many; color: Red. Hairs—many; color: Red.
*Branches.*—Color—Dull Green. Thorns — many; long; straight; with oval base. Prickles—many; color: Reddish. Hairs—none.
*New shoots.*—Color—Dull Red. Thorns—many; long; straight; with long base. Prickles—many; color: Reddish. Hairs—none.

I claim:

A new and distinct variety of rose plant of the hybrid tea class, substantially as herein shown and described, characterized particularly as to novelty by the unique combination of a vigorous habit of growth, exceeding that of the seed parent "Arles," a very free blooming habit, a two-toned appearance of the flower buds, large size of the open flowers, exceeding that of the pollen parent "Mignonne," a satiny and hard texture of the flower petals, and a distinctive, attractive, soft but clear blending of the flower color from the tips of the petals to the base thereof when the buds open, with the color having the general appearance of one color, corresponding to Bright Carmine Rose when the flowers mature.

No references cited.

ABRAHAM G. STONE, *Primary Examiner.*